Figure 1:
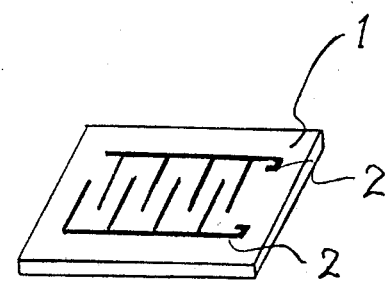

United States Patent [19]

Nitta et al.

[11] 4,015,230
[45] Mar. 29, 1977

[54] HUMIDITY SENSITIVE CERAMIC RESISTOR

[75] Inventors: Tsuneharu Nitta, Katano; Ziro Terada, Yao; Shigeru Hayakawa, Hirakata, all of Japan

[73] Assignee: Matsushita Electric Industrial Co., Ltd., Japan

[22] Filed: Jan. 27, 1976

[21] Appl. No.: 652,702

[30] Foreign Application Priority Data

Feb. 3, 1975   Japan ............................... 50-14508
Feb. 17, 1975  Japan ............................... 50-20136
Feb. 12, 1975  Japan ............................... 50-18244

[52] U.S. Cl. ............................... 338/35; 23/254 E; 338/308; 338/314
[51] Int. Cl.² ............................... H01L 7/00
[58] Field of Search ............. 338/35, 34, 307, 308, 338/309, 314; 200/61.06, 61.04; 340/235; 324/65 M; 73/27 R, 73, 838; 23/254 E, 255 E; 252/515, 518; 427/101, 102, 126

[56] References Cited
UNITED STATES PATENTS 3,748,625   7/1973   Bennewitz ........................... 338/34
3,864,659   2/1975   Furauchi et al. ..................... 338/35
3,961,301   6/1976   Fraioli ............................... 338/35

*Primary Examiner*—C. L. Albritton
*Attorney, Agent, or Firm*—Wenderoth, Lind & Ponack

[57] ABSTRACT

Humidity sensitive ceramic resistor having a high humidity activity, a low electrical resistance and a high stability with respect to time, temperature, humidity and electric load and suited for use in humidity-controlling devices is provided by a sintered mixture of a main component, which consists essentially of chromium oxide and at least one metal oxide selected from the group consisting of $TiO_2$, $ZrO_2$, $HfO_2$, $SnO_2$, $Nb_2O_5$, $Ta_2O_5$, $WO_3$, $MnO_2$, $MoO_2$, $CeO_2$, $DyO_2$, $VO_2$, $SiO_2$ and $GeO_2$, and an addition of at least one metal oxide selected from the group consisting of BeO, MgO, CaO, SrO, BaO, FeO, NiO, CuO, ZnO, CdO and PbO. Furthermore, humidity sensitive thin layer ceramic resistor having an improved quick response to humidity is obtained by sintering a mixture having the above composition with a glass frit binder.

17 Claims, 3 Drawing Figures

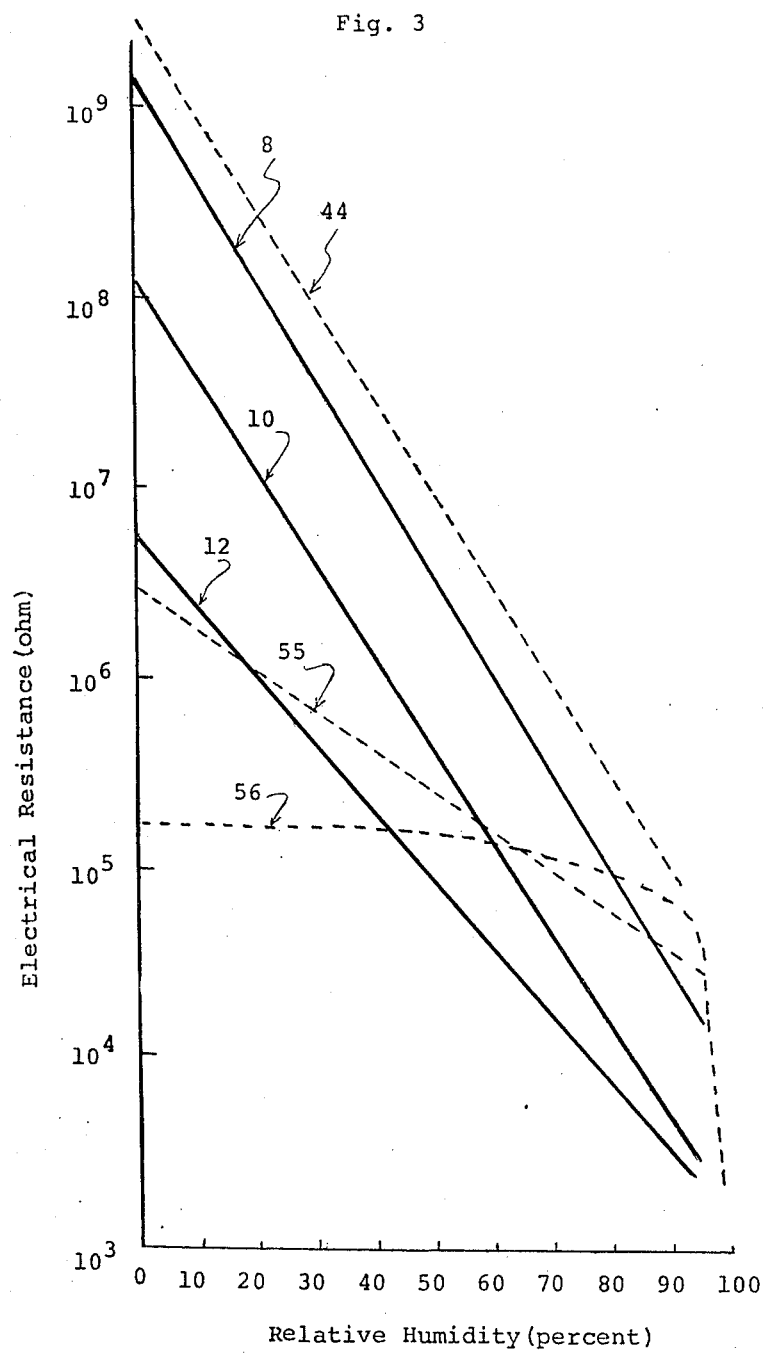

HUMIDITY SENSITIVE CERAMIC RESISTOR

This invention relates to a humidity sensitive resistor, and more particularly it relates to a novel humidity sensitive ceramic resistor of semiconductive ceramic composition comprising a chromium oxide component.

Recently, the electronic industry has required the provision of humidity sensitive semiconductors suitable for making humidity controlling devices operating over a wide range of relative humidity, i.e., from 0 to 100 percent. It is important in making such devices, that the humidity sensitive materials have a high humidity activity, a low electrical resistance, and a small variation of these characteristics with time.

In prior art, there are known humidity sensitive semiconductive materials such as magnetite, germanium, selenium, potassium metaphosphate or the like. However, the conventional materials such as magnetite, germanium or selenium have a disadvantage in that a response rate thereof to humidity is very slow. For example, a magnetite thin film takes two minutes to respond to a change of relative humidity from 60 to 98 percent. On the other hand, while a potassium metaphosphate thin film responds as quickly as two seconds to a change of relative humidity from 80 to 33 percent, it has a disadvantage that the characteristics thereof varied greatly with time. Further, these conventional humidity sensitive resistors have other problems such as narrow range of relative humidity to which the resistors can respond, lack of uniformity of characteristics, high cost, etc.

In contrast to the above semiconductive materials, there are known humidity sensitive resistors comprising metal oxide ceramic materials as aluminum oxide, chromium oxide, nickel oxide or the like having a very quick response to humidity, and they have advantages of ease of forming into a desired shape and suitability for mass production. However, these conventional ceramic materials usually have a high electrical resistance, i.e., above $10^{13}\Omega$ at 0 percent relative humidity, and they are not suitable for low humidity sensitive resistors. For example, a humidity resistor of aluminum oxide or chromium oxide covers a narrow range of relative humidity from 80 to 100 percent with variations of electrical resistance from 1000 M$\Omega$ to 1 M$\Omega$. In addition, these ceramic materials undesirably have a hysteresis characteristic to relative humidity vs. electrical resistance curve.

Although many efforts have been directed to the concurrent improvement of all of these characteristics, entirely satisfactory results have not been obtained with the conventional humidity sensitive resistors.

Accordingly, a principle object of the present invention is to provide a novel and improved humidity sensitive ceramic resistor having a low electrical resistance, high humidity activity and a quick response rate to a humidity with composition of semiconductive chromium oxide ceramic.

A further object of the present invention is to provide a novel humidity sensitive thin layer ceramic resistor having low electrical resistance, high humidity activity and quick response to a humidity.

A still further object of the present invention is to provide a novel humidity sensitive ceramic resistor having a high stability with respect to time, atmosphere, temperature and electric load and being produced with low cost.

Such a humidity sensitive ceramic resistor provided according to this invention is suitable for use in air conditioners, dew-point protectors, cooking controllers, etc.

These objects of the invention are realized by providing a humidity sensitive ceramic resistor which comprises a ceramic plate having a conducting electrode secured to a surface thereof; said ceramic plate consisting essentially of, as solid ingredients, more than 98 to 99.95 percent by weight of a main component consisting essentially of 99.99 to 80 percent by mole of chromium oxide ($Cr_2O_3$) and 0.01 to 20 percent by mole of at least one metal oxide selected from the group consisting of titanium oxide, zirconium oxide, hafnium oxide, tin oxide, niobium oxide, tantalum oxide, tungsten oxide, manganese oxide, molybdenum oxide, cerium oxide, dysprosium oxide, vanadium oxide, silicon oxide and germanium oxide; and 0.05 to less than 2 percent by weight of an addition of at least one metal oxide selected from the group consisting of beryllium oxide, magnesium oxide, calcium oxide, strontium oxide, barium oxide, iron oxide, nickel oxide, copper oxide, zinc oxide, cadmium oxide and lead oxide.

Figure 2:
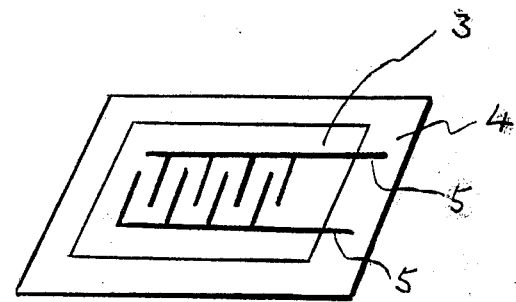

These and other objects and the features of this invention will become apparent upon consideration of the following detailed description taken together with the accompanying drawings in which;

FIGS. 1 and 2 are plan views of a preferred embodiment of the present invention; and FIG. 3 is graph illustrating the electrical resistance at varying relative humidities of the humidity sensitive ceramic resistor shown in FIGS. 1 and 2.

Proceeding to the detailed description of the present invention, the construction of a humidity sensitive ceramic resistor according to the present invention will be explained with reference to FIG. 1, wherein a semiconductive ceramic plate designated by a reference numeral 1 has interdigital electrodes 2 applied to one surface thereof. The ceramic plate consists essentially of, as solid ingredients, more than 98 to 99.95 percent by weight of main component consisting essentially of 99.99 to 80 percent by mole of chromium oxide ($Cr_2O_3$) and 0.01 to 20 percent by mole of at least one metal oxide selected from the group consisting of titanium, zirconium, hafnium, tin, niobium, tantalum, tungsten, manganese, molybdenum, cerium, dysprosium, vanadium, silicon and germanium, and 0.05 to less than 2 percent by weight of an addition of at least one metal oxide selected from the group consisting of beryllium, magnesium, calcium, strontium, barium, iron, nickel, copper, zinc, cadmium and lead.

The component oxides are intimately mixed in the desired compositional proportions and fired in accordance with a schedule set forth hereinafter for production of a fired ceramic body. The ceramic resistors containing the composition within the range of the present invention desirably show a low electrical resistance and a high humidity activity. On the other hand, it has been found by experiments that a ceramic resistor containing more than 99.95 percent by mole of chromium oxide in the main component has a humidity activity as low as a ceramic containing only chromium oxide. Further, it is found that a decrease in the proportion of chromium oxide below 80 mole percent results in a lower humidity activity. Moreover, variation by way of a decrease from 0.05 percent by weight of an addition of at least one metal oxide selected from the group consisting of beryllium, magnesium, calcium, strontium, barium, iron, nickel, copper, zinc, cadmium and lead results in a high electrical resistance. On the other hand, an increase in the proportion of said addition above 2 percent by weight results in a low humidity activity. Among said various additions, magnesium oxide, iron oxide, nickel oxide and zinc oxide are preferred ones because their use results in a lower electrical resistance and a higher humidity activity.

It has been discovered according to the present invention that said electrode 2 comprising a semiconductive material having a lower electrical resistance than that of said ceramic plate 1 produces a humidity sensitive resistor characterized by a high stability during a load life test at a high temperature. The electrodes 2 can be formed of any suitable metal oxide such as ruthenium oxide, nickel oxide, tin oxide, indium oxide, cadmium oxide, titanium oxide, zinc oxide, barium titanate or barium metaplumbate, and the electrodes are prepared by any suitable method, for example, by a stencil or spray method. Among these metal oxides, ruthenium oxide, tin oxide and indium oxide result in the best electrode.

FIG. 2 shows another embodiment of the invention, wherein a semiconductive thin layer ceramic film 3 is coated on an insulating ceramic substrate 4, and interdigital electrodes 5 are applied to the surface of the film 3. Said ceramic film 3 consists essentially of 97 to 20 percent by weight of humidity sensitive resistor component and 3 to 80 percent by weight of glass frit binder. Said humidity sensitive resistor component consists essentially of, as solid ingredients, 99.50 to 80 percent by weight of main component consisting essentially of 99.99 to 80 percent by mole of chromium oxide and 0.01 to 20 percent by mole of at least one metal oxide selected from the group consisting of titanium, zirconium, hafnium, tin, niobium, tantalum, tungsten, manganese, molybdenum, cerium, dysprosium, vanadium, silicon and germanium, and 0.05 to 20 percent by weight of an addition of at least one metal oxide selected from the group consisting of beryllium, magnesium, calcium, strontium, barium, iron, nickel, copper, zinc, cadmium and lead.

It has been discovered according to the present invention that the resultant humidity sensitive resistor comprising said ceramic film component exhibits a high humidity activity, a low electrical resistance and an improved response humidity. The properties are attributed to the characteristics of said humidity sensitive resistor component and the poor reaction of said humidity sensitive resistor with glass frit binder.

The preferred glass frit is selected from the group consisting of lead silicate, boron silicate, lead boron silicate and lead boron silicate containing at least one metal oxide selected from the group consisting of alkali earth metals, zinc and cadmium. It is found that a ceramic resistor containing below 3 percent by weight of said glass frit binder results in a poor adhesion to an insulating ceramic substrate, and an increase in the proportion of said glass frit binder above 80 percent by weight results in higher electrical resistance and lower humidity activity.

The thin layer ceramic film of the present invention can be prepared by a per se well known fabrication method. The said humidity sensitive resistor components in powder form are intimately mixed and fired in air. The humidity sensitive resistor component powder with glass frit binder is mixed with an organic binder for producing a paste. The paste is coated onto an insulating ceramic substrate 4 by stencil, brush or spray method, and it is dried and sintered at 800° to 1300° C. During the drying and sintering, the organic binder evaporates.

The electrode 5 can be also formed in per se conventional manner, for example, firing-on. Said electrode is preferably selected from compounds of ruthenium oxide, nickel oxide, tin oxide, indium oxide, cadmium oxide, titanium oxide, zinc oxide, barium titanate and barium metaplumbate, which are semiconductive materials characterized by having a lower electrical resistance than that of said thin layer ceramic film 3.

The following examples of preferred embodiments are given by way of illustration and should not be construed as limitative.

EXAMPLE I

Semiconductive ceramics for humidity sensitive resistor were made in a per se conventional manner with the composition as shown in Table 1. The raw materials used for the ceramics were commercially pure grade chromium oxide ($Cr_2O_3$), titanium oxide ($TiO_2$), zirconium oxide ($ZrO_2$), hafnium oxide ($HfO_2$) tin oxide ($SnO_2$) niobium oxide ($Nb_2O_5$), tantalum oxide ($Ta_2O_5$), tungaten oxide ($WO_3$), manganese oxide ($MnO_2$), molybdenum oxide ($MoO_2$), cerium oxide ($CeO_2$), dysprosium oxide ($DyO_2$), vanadium oxide ($VO_2$), silicon oxide ($SiO_2$), germanium oxide ($GeO_2$), beryllium oxide (BeO), magnesium oxide (MgO), calcium oxide (CaO), iron oxide (FeO), nickel oxide (NiO), copper oxide (CuO), zinc oxide (ZnO) and cadmium oxide (CdO), and reagent grade strontium carbonate ($SrCO_3$) and barium carbonate ($BaCO_3$). It should be noted that any compound which is converted upon firing to the corresponding oxide can be used as a raw material.

Batches of raw materials were ball milled with water for intimate mixing and then dried. The powder was admixed with an emulsion of polyvinyl alcohol in a proportion of 100 grams of the powder to 12 cc of 6 percent aqueous emulsion of polyvinyl alcohol. The powder mixture was then pressed at a 750 kg/cm² into rectangular plates of 24 × 13 mm in length and 1 mm in thickness. The plates were sintered in air at 1350° C for 2 hours, while being supported on alumina plates. These sintered plates were then provided, on one surface, with interdigital electrodes. Ruthenium oxide paste was fired at 800° C on the plate surface to form electrodes in a per se conventional manner. As a reference, silver electrode was coated with silver paint.

Then, humidity properties were measured by a per se well-known method for the resultant humidity sensitive ceramic resistor. Electrical resistance was measured by applying a field of 10 V (A.C.).

Humidity activity was obtained by measuring electrical resistance over a range of relative humidity of 0 percent to 100 percent at 20° C. The activity ($\alpha$) is computed from electrical resistance in relative humidity of 0 percent ($R_0$%) and electrical resistance in relative humidity of 95 percent ($R_{95}$ %).

Load life test was carried out in a thermostat at 80° C and more than 95 percent (relative humidity) by applying a current of 10 milliamperes for 5000 hours, and the varation in the value of $R_0$% and $R_{95}$% was expressed by the electrical resistance.

The measured humidity properties of the resultant humidity sensitive ceramic resistors are shown in Table 1. As apparent from Table 1, simultaneous addition of both of the metal oxide (the first addition) to main component and another metal oxide as the additive (the second addition) results in higher humidity activity, lower electrical resistance and higher stability with respect to time, temperature humidity and electric load than in the case of a mere addition of the first addition to main component without said second addition or a mere addition of said second addition to the main component having no first addition. In addition, as shown in Table 1, chromium oxide only results in poor humidity activity.

The humidity dependence of the electrical resistance of the resultant resistors is shown by solid lines in FIG. 3. As shown in FIG. 3, the humidity sensitive ceramic resistor according to the invention has nearly linear relative humidity vs. logarithm electrical resistance characteristics.

EXAMPLE 2

Now, the humidity sensitive thin layer ceramic resistor of the present invention was prepared and comprised a mixture of fine particles of a humidity sensitive component similar to that described in Example 1 and a glass frit. The raw materials used were commercialy pure grade $Cr_2O_3$, $TiO_2$, $ZrO_2$, $NfO_2$, $Ta_2O_5$, $DyO_2$, $SiO_2$, $MgO$, $CaO$, $FeO$, $NiO$, $ZnO$ and $PbO$. The preparation of the humidity sensitive components was by a well known method. That is, batches of the raw materials were ball milled with water for intimate mixing and then dried. After that, the powder mixture were put into alumina crucible and fired in air at 1350° C for 2 hours.

The glass frit used in the humidity sensitive thin layer ceramic resistor of the present invention was a well known lead silicate composition consisting of 30 percent by mole of $PbO$ and 70 percent by mole of $SiO_2$.

The preparation of such glass frit was by a well known method. That is, the constituents were melted in air at 1350° C for 1 hour and the molten composition was poured into water to form the frit. The coarse frit was milled in a ball mill with water to reduce the particle size of the frit and to obtain a frit of substantially uniform size.

For making the humidity sensitive thin layer ceramic resistor of the present invention, the humidity sensitive component and the glass frit provided as described above were broken down by ball milling with water to a substantially uniform particle size. The average particle size was below 2 microns. The powders were thoroughly mixed together by rolling in an organic binder such as a mixture of butyl carbitol acetate and polyester resin. By adding or removing the liquid binder, the mixtures were then adjusted to the proper viscosity for applying the resistance material to a substrate. The resultant paste of the humidity sensitive resistance material was applied to a uniform thickness of 40~60 microns on the surface of alumina substrate by screen stencil application. The size was 12 × 20 mm in length. The substrates with the resistance materials were then fired in a conventional furnace in air at 1200° C for 2 hours and then cooled at "furnace power off." Then, ruthenium oxide paste was fired at 800° C on the sintered thin layer surface to form interdigital electrodes in per se conventional manner.

Humidity properties were measured in the same manner as previously described in Example 1. In addition, response rate to a humidity was measured by changing the relative humidity from 95 to 50%. The measured humidity properties of the resultant humidity sensitive thin layer ceramic resistor are shown in Table 2. As apparent from Table 2, the thin layer ceramic resistor of the present invention shows excellent characteristics of high humidity activity, low electrical resistance, quick response to a humidity and stability with time, temperature, humidity and electric load.

The humidity dependence of the electrical resistance of the resultant resistors is shown by the dotted line in FIG. 3. As apparent from FIG. 3, the thin layer ceramic resistors are divided into two types; the first type having a linear characteristic over a range of relative humidity from 0 percent to 100 percent, and the second type having a non-linear characteristic characterized by a sudden decrease of electrical resistance from a relatively constant resistance to a extremely low resistance in a range of high relative humidity of several dozens percent.

Table 1

| Sample Number | Ceramic Composition | | | | Humidity Properties | | | | |
|---|---|---|---|---|---|---|---|---|---|
| | Main component (mole percent) | | Main component (weight percent) | Additive | $R_0\%$ ($\Omega$) | $R_{95}\%$ ($\Omega$) | $\alpha$ | Varied value after Load Life Test | |
| | | | | | | | | $R_0\%(\Omega)$ | $R_{95}\%(\Omega)$ |
| 1* | $Cr_2O_3$ | 100 | 100 | — | $1.2\times10^{14}$ | $2.4\times10^9$ | $5\times10^4$ | $1.4\times10^{14}$ | $4.2\times10^{12}$ |
| 2* | $Cr_2O_3$ $TiO_2$ | 98 2.0 | 100 | — | $1.3\times10^{13}$ | $3.2\times10^7$ | $4.06\times10^5$ | $2.6\times10^{13}$ | $3.8\times10^9$ |
| 3* | $Cr_2O_3$ $TiO_2$ | 99.995 0.005 | 99.0 | MgO 1.0 | $4.2\times10^5$ | $2.6\times10^5$ | $1.6\times10^0$ | $3.7\times10^6$ | $3.6\times10^6$ |
| 4* | $Cr_2O_3$ $TiO_2$ | 78.0 22.0 | 99.0 | MgO 1.0 | $3.2\times10^8$ | $2.7\times10^7$ | $1.2\times10^1$ | $3.8\times10^8$ | $3.4\times10^8$ |
| 5* | $Cr_2O_3$ | 100 | 99.0 | MgO 1.0 | $2.4\times10^5$ | $1.3\times10^5$ | $1.8\times10^0$ | $5.7\times10^6$ | $5.3\times10^6$ |
| 6* | $Cr_2O_3$ $TiO_2$ | 98.0 2.0 | 99.99 | MgO 0.01 | $1.4\times10^{13}$ | $3.3\times10^7$ | $4.2\times10^5$ | $2.5\times10^{13}$ | $3.7\times10^9$ |
| 7 | $Cr_2O_3$ $TiO_2$ | 98.0 2.0 | 99.95 | MgO 0.05 | $2.8\times10^{10}$ | $3.2\times10^4$ | $8.8\times10^5$ | $2.8\times10^{10}$ | $3.5\times10^4$ |
| 8 | $Cr_2O_3$ $TiO_2$ | 98.0 2.0 | 99.90 | MgO 0.1 | $1.4\times10^9$ | $2.6\times10^4$ | $9.2\times10^4$ | $1.4\times10^9$ | $9.6\times10^4$ |
| 9 | $Cr_2O_3$ $TiO_2$ | 98.0 2.0 | 99.5 | MgO 0.5 | $1.8\times10^9$ | $1.4\times10^4$ | $1.3\times10^5$ | $1.8\times10^9$ | $1.5\times10^4$ |
| 10 | $Cr_2O_3$ $TiO_2$ | 98.0 2.0 | 99.0 | MgO 1.0 | $1.2\times10^8$ | $3.2\times10^3$ | $3.8\times10^4$ | $1.2\times10^8$ | $3.4\times10^4$ |

Table 1-continued

| Sample Number | Ceramic Composition Main component (mole percent) | | Main component (weight percent) | Additive | $R_0\%$ ($\Omega$) | $R_{95}\%$ ($\Omega$) | $\alpha$ | Varied value after Load Life Test $R_0\%(\Omega)$ | $R_{95}\%(\Omega)$ |
|---|---|---|---|---|---|---|---|---|---|
| 11 | TiO$_2$ Cr$_2$O$_3$ | 2.0 98.0 | 98.5 | MgO 1.5 | $6.4\times10^7$ | $2.8\times10^3$ | $2.3\times10^4$ | $6.4\times10^7$ | $2.8\times10^3$ |
| 12 | TiO$_2$ Cr$_2$O$_3$ | 2.0 98.0 | 98.2 | MgO 1.8 | $5.2\times10^6$ | $2.2\times10^3$ | $2.4\times10^3$ | $5.2\times10^6$ | $2.2\times10^7$ |
| 13* | TiO$_2$ Cr$_2$O$_3$ | 2.0 98.0 | 98.0 | MgO 2.0 | $1.3\times10^5$ | $1.8\times10^3$ | $7.2\times10^1$ | $1.3\times10^6$ | $1.9\times10^5$ |
| 14 | TiO$_2$ Cr$_2$O$_3$ | 2.0 98.0 | 99.5 | BeO 0.5 | $8.0\times10^9$ | $6.2\times10^4$ | $1.3\times10^5$ | $8.0\times10^9$ | $6.2\times10^4$ |
| 15 | TiO$_2$ Cr$_2$O$_3$ | 2.0 98.0 | 99.5 | CaO 0.5 | $8.0\times10^9$ | $6.2\times10^4$ | $1.3\times10^5$ | $8.0\times10^9$ | $6.2\times10^4$ |
| 16 | TiO$_2$ Cr$_2$O$_3$ | 2.0 98.0 | 99.5 | SrO 0.5 | $9.0\times10^9$ | $6.0\times10^4$ | $1.5\times10^5$ | $8.8\times10^9$ | $6.\times10^4$ |
| 17 | TiO$_2$ Cr$_2$O$_3$ | 2.0 98.0 | 99.5 | BaO 0.5 | $8.0\times10^9$ | $6.0\times10^4$ | $1.3\times10^5$ | $8.0\times10^9$ | $6.0\times10^4$ |
| 18 | TiO$_2$ Cr$_2$O$_3$ | 2.0 98.0 | 99.5 | FeO 0.5 | $1.6\times10^9$ | $1.2\times10^4$ | $1.3\times10^5$ | $1.6\times10^9$ | $1.2\times10^4$ |
| 19 | TiO$_2$ Cr$_2$O$_3$ | 2.0 98.0 | 99.5 | NiO 0.5 | $1.6\times10^9$ | $1.2\times10^4$ | $1.3\times10^5$ | $1.7\times10^9$ | $1.3\times10^4$ |
| 20 | TiO$_2$ Cr$_2$O$_3$ | 2.0 98.0 | 99.5 | CuO 0.5 | $7.8\times10^9$ | $5.8\times10^4$ | $1.3\times10^5$ | $7.8\times10^9$ | $5.3\times10^4$ |
| 21 | TiO$_2$ Cr$_2$O$_3$ | 2.0 98.0 | 99.5 | ZnO 0.5 | $1.7\times10^9$ | $1.6\times10^4$ | $1.1\times10^5$ | $1.7\times10^9$ | $1.6\times10^4$ |
| 22 | TiO$_2$ Cr$_2$O$_3$ | 2.0 98.0 | 99.5 | CdO 0.5 | $8.0\times10^9$ | $6.0\times10^4$ | $1.3\times10^5$ | $8.0\times19^9$ | $6.0\times10^4$ |
| 23 | TiO$_2$ Cr$_2$O$_3$ | 2.0 98.0 | 99.5 | PbO 0.5 | $8.0\times10^9$ | $6.0\times10^4$ | $1.3\times10^5$ | $8.0\times10^9$ | $6.2\times10^4$ |
| 24 | ZrO$_2$ Cr$_2$O$_3$ | 2.0 98.0 | 99.5 | MgO 0.5 | $1.7\times10^9$ | $1.3\times10^4$ | $1.3\times10^5$ | $1.8\times10^9$ | $1.4\times10^4$ |
| 25 | NfO$_2$ Cr$_2$O$_3$ | 2.0 98.0 | 99.5 | MgO 0.5 | $1.8\times10^9$ | $1.4\times10^4$ | $1.3\times10^5$ | $1.8\times10^9$ | $1.5\times10^4$ |
| 26 | SnO$_2$ Cr$_2$O$_3$ | 2.0 98.0 | 99.5 | MgO 0.5 | $1.6\times10^9$ | $1.2\times10^4$ | $1.3\times10^5$ | $1.6\times10^9$ | $1.2\times10^4$ |
| 27 | Nb$_2$O$_5$ Cr$_2$O$_3$ | 2.0 98.0 | 99.5 | MgO 0.5 | $1.6\times10^9$ | $1.2\times10^4$ | $1.3\times10^5$ | $1.6\times10^9$ | $1.2\times10^4$ |
| 28 | Ta$_2$O$_5$ Cr$_2$O$_3$ | 2.0 98.0 | 99.5 | MgO 0.5 | $1.6\times10^9$ | $1.2\times10^4$ | $1.3\times10^5$ | $1.6\times10^9$ | $1.2\times10^4$ |
| 29 | WO$_3$ Cr$_2$O$_3$ | 2.0 98.0 | 99.5 | MgO 0.5 | $1.8\times10^9$ | $1.4\times10^4$ | $1.3\times10^5$ | $1.8\times10^9$ | $1.0\times10^4$ |
| 30 | MnO$_2$ Cr$_2$O$_3$ | 2.0 98.0 | 99.5 | MgO 0.5 | $1.6\times10^9$ | $1.2\times10^4$ | $1.3\times10^5$ | $1.6\times10^9$ | $1.2\times10^4$ |
| 31 | MoO$_2$ Cr$_2$O$_3$ | 2.0 98.0 | 99.5 | MgO 0.5 | $1.8\times10^9$ | $1.4\times10^4$ | $1.3\times10^5$ | $1.8\times10^9$ | $1.4\times10^4$ |
| 32 | CeO$_2$ Cr$_2$O$_3$ | 2.0 98.0 | 99.5 | MgO 0.5 | $1.8\times10^9$ | $1.4\times10^4$ | $1.3\times10^5$ | $1.8\times10^9$ | $1.4\times10^4$ |
| 33 | DyO$_2$ Cr$_2$O$_3$ | 2.0 98.0 | 99.5 | MgO 0.5 | $1.8\times10^9$ | $1.4\times10^4$ | $1.3\times10^5$ | $1.8\times10^9$ | $1.4\times10^4$ |
| 34 | VO$_2$ Cr$_2$O$_3$ | 2.0 98.0 | 99.5 | MgO 0.5 | $1.7\times10^9$ | $1.3\times10^4$ | $1.3\times10^5$ | $1.7\times10^9$ | $1.3\times10^4$ |
| 35 | GeO Cr$_2$O$_3$ | 2.0 98.0 | 99.5 | MgO 0.5 | $1.8\times10^9$ | $1.4\times10^4$ | $1.3\times10^5$ | $1.8\times10^9$ | $1.4\times10^4$ |
| 36 | TiO$_2$ Cr$_2$O$_3$ | 4.0 96.0 | 99.5 | MgO 0.5 | $2.4\times10^9$ | $2.2\times10^4$ | $1.1\times10^5$ | $2.5\times10^9$ | $2.3\times10^4$ |
| 37 | TiO$_2$ Cr$_2$O$_3$ | 10.0 90.0 | 99.5 | MgO 0.5 | $2.8\times10^9$ | $3.2\times10^4$ | $8.8\times10^4$ | $2.2\times10^9$ | $3.2\times10^4$ |
| 38 | TiO$_2$ Cr$_2$O$_3$ | 15.0 85.0 | 99.5 | MgO 0.5 | $2.8\times10^9$ | $4.8\times10^4$ | $5.8\times10^4$ | $2.8\times10^9$ | $4.8\times10^4$ |
| | TiO$_2$ Cr$_2$O$_3$ | 15.0 80.0 | | | | | | | |

Table 1-continued

| Sample Number | Ceramic Composition Main component (mole percent) | | Main component (weight percent) | Additive | Humidity Properties $R_0\%$ ($\Omega$) | $R_{95}\%$ ($\Omega$) | $\alpha$ | Varied value after Load Life Test $R_0\%(\Omega)$ | $R_{95}\%$ ($\Omega$) |
|---|---|---|---|---|---|---|---|---|---|
| 39 | TiO$_2$ | 20.0 | 99.5 | MgO 0.5 | $2.7\times10^9$ | $7.2\times10^5$ | $3.8\times10^3$ | $2.7\times10^9$ | $7.2\times10^5$ |

(*outside the invention)

Table 2

| Sample Number | Humidity Sensitive component Main Component (mole percent) | | additive (weight Percent) | Thin Layer $10^9$ (weight percent) Humidity sensitive component | Glass frit | Humidity Properties $R_0\%$ | $R_{95}\%$ | $\alpha$ | Varied Value after Life Test $R_0\%$ | $R_{95}\%$ | Response Rate (second) |
|---|---|---|---|---|---|---|---|---|---|---|---|
| 40 | Cr$_2$O$_3$ TiO$_2$ | 98.0 2.0 | MgO 1.0 | 98.2 | 2.0 | $1.8\times10^5$ | $1.7\times10^4$ | $1.1\times10$ | $4.7\times10^5$ | $3.2\times10^5$ | 12 |
| 41 | Cr$_2$O$_3$ TiO$_2$ | 98.0 2.0 | MgO 1.0 | 97.0 | 3.0 | $1.2\times10^8$ | $3.2\times10^4$ | $3.8\times10^3$ | $1.3\times10^8$ | $3.6\times10^4$ | 4.5 |
| 42 | Cr$_2$O$_3$ TiO$_2$ | 98.0 2.0 | MgO 1.0 | 95.0 | 5.0 | $1.7\times10^5$.-$3\times10^4$ | $3.2\times10^4$ | $1.7\times10^9$ | $3.2\times10^4$ | | 2.5 |
| 43 | Cr$_2$O$_3$ TiO$_2$ | 98.0 2.0 | MgO 1.0 | 90.0 | 10.0 | $2.3\times10^9$ | $6.0\times10^4$ | $3.8\times10^4$ | $2.3\times10^9$ | $6.0\times10^4$ | 1.5 |
| 44 | Cr$_2$O$_3$ TiO$_2$ | 98.0 2.0 | MgO 1.0 | 80.0 | 20.0 | $3.0\times10^9$ | $6.0\times10^4$ | $5.0\times10^4$ | $3.0\times10^9$ | $6.0\times10^4$ | 1.0 |
| 45 | Cr$_2$O$_3$ TiO$_2$ | 98.0 2.0 | MgO 1.0 | 70.0 | 30.0 | $3.1\times10^9$ | $6.0=10^4$ | $5.2\times10^4$ | $3.1\times10^9$ | $6.0\times10^4$ | 1.0 |
| 46 | Cr$_2$O$_3$ TiO$_2$ | 98.0 2.0 | MgO 1.0 | 60.0 | 40.0 | $3.5\times10^9$ | $7.0\times10^4$ | $5.0\times10^4$ | $3.5\times10^9$ | $7.1\times10^4$ | 1.0 |
| 47 | Cr$_2$O$_3$ TiO$_2$ | 98.0 2.0 | MgO 1.0 | 50.0 | 50.0 | $4.0\times10^9$ | $9.0\times10^4$ | $4.4\times10^4$ | $4.0\times10^9$ | $9.2\times10^4$ | 1.0 |
| 48 | Cr$_2$O$_3$ TiO$_2$ | 98.0 2.0 | MgO 1.0 | 40.0 | 60.0 | $4.6\times10^9$ | $1.1\times10^5$ | $4.2\times10^4$ | $4.6\times10^9$ | $1.2\times10^5$ | 1.0 |
| 49 | Cr$_2$O$_3$ TiO$_2$ | 98.0 2.0 | MgO 1.0 | 30.0 | 70.0 | $4.8\times10^9$ | $1.7\times10^5$ | $2.8\times10^4$ | $4.9\times10^9$ | $1.8\times10^5$ | 1.0 |
| 50 | Cr$_2$O$_3$ TiO$_2$ | 98.0 2.0 | mgO 1.0 | 25.0 | 75.0 | $4.5\times10^9$ | $2.8\times10^5$ | $1.6\times10^4$ | $4.5\times10^9$ | $2.8\times10^5$ | 1.0 |
| 51 | Cr$_2$O$_3$ TiO$_2$ | 98.0 2.0 | MgO 1.0 | 20.0 | 80.0 | $6.4\times10^9$ | $4.6\times10^6$ | $1.4\times10^3$ | $6.4\times10^9$ | $4.6\times10^6$ | 1.0 |
| *52 | Cr$_2$O$_3$ TiO$_2$ | 98.0 2.0 | MgO 1.0 | 18.0 | 82.0 | $2.9\times10^{10}$ | $1.6\times10^{10}$ | 1.8 | $2.9\times10^{10}$ | $1.6\times10^{10}$ | 1.0 |
| *53 | Cr$_2$O$_3$ TiO$_2$ | 98.0 2.0 | MgO 0.03 | 75.0 | 25.0 | $2.7\times10^{13}$ | $6.5\times10^7$ | $4.2\times10^5$ | $3.6\times10^{13}$ | $5.1\times10^9$ | 1.0 |
| 54 | Cr$_2$O$_3$ TiO$_2$ | 98.0 2.0 | MgO 0.05 | 75.0 | 25.0 | $3.9\times10^{11}$ | $1.3\times10^6$ | $3.0\times10^5$ | $4.1\times10^{11}$ | $1.5\times10^6$ | 1.0 |
| 55 | Cr$_2$O$_3$ TiO$_2$ | 98.0 2.0 | MgO 2.0 | 75.0 | 25.0 | $2.4\times10^6$ | $3.2\times10^4$ | $7.5\times10$ | $2.4\times10^6$ | $3.2\times10^4$ | 0.5 |
| 56 | Cr$_2$O$_3$ TiO$_2$ | 98.0 2.0 | MgO 10.0 | 75.0 | 25.0 | $1.8\times10^5$ | $1.7\times10^4$ | $1.1\times10$ | $1.8\times10^5$ | $1.7\times10^4$ | 0.5 |
| 57 | Cr$_2$O$_3$ TiO$_2$ | 98.0 2.0 | MgO 20.0 | 75.0 | 25.0 | $2.0\times10^5$ | $1.8\times10^4$ | $1.1\times10$ | $2.0\times10^5$ | $1.8\times10^4$ | 0.5 |
| *58 | Cr$_2$O$_3$ TiO$_2$ | 98.0 2.0 | MgO 22.0 | 75.0 | 25.0 | $1.9\times10^5$ | $1.0\times10^5$ | 1.9 | $2.9\times10^5$ | $1.8\times10^5$ | 0.5 |
| 59 | Cr$_2$O$_3$ TiO$_2$ | 98.0 2.0 | CaO 1.0 | 75.0 | 25.0 | $9.0\times10^9$ | $1.6\times10^5$ | $5.6\times10^4$ | $9.0\times10^9$ | $1.6\times10^5$ | 1.0 |
| 60 | Cr$_2$O$_3$ TiO$_2$ | 98.0 2.0 | NiO 1.0 | 75.0 | 25.0 | $5.4\times10^9$ | $1.0\times10^5$ | $5.4\times10^4$ | $5.4\times10^9$ | $1.0\times10^5$ | 1.0 |
| 61 | Cr$_2$O$_3$ TiO$_2$ | 98.0 2.0 | ZnO 1.0 | 75.0 | 25.0 | $3.4\times10^9$ | $8.5\times10^4$ | $4.0\times10^4$ | $3.4\times10^9$ | $8.5\times10^4$ | 1.0 |
| 62 | Cr$_2$O$_3$ TiO$_2$ | 98.0 2.0 | FeO 1.0 | 75.0 | 25.0 | $2.4\times10^9$ | $5.7\times10^4$ | $4.2\times10^4$ | $2.4\times10^9$ | $5.8\times10^4$ | 1.0 |
| 63 | Cr$_2$O$_3$ ZrO$_2$ | 98.0 2.0 | MgO 1.0 | 75.0 | 25.0 | $2.8\times10^9$ | $6.2\times10^4$ | $4.5\times10^4$ | $2.8\times10^9$ | $6.3\times10^4$ | 1.0 |
| 64 | Cr$_2$O$_3$ HfO$_2$ | 98.0 2.0 | MgO 1.0 | 75.0 | 25.0 | $3.2\times10^9$ | $6.4\times10^4$ | $5.0\times10^4$ | $3.2\times10^9$ | $6.4\times10^4$ | 1.0 |
| 65 | Cr$_2$O$_3$ Ta$_2$O$_5$ | 98.0 2.0 | MgO 1.0 | 75.0 | 25.0 | $3.4\times10^9$ | $6.4\times10^4$ | $5.0\times10^4$ | $3.4\times10^9$ | $6.4\times10^4$ | 1.0 |
| 66 | Cr$_2$O$_3$ DyO$_2$ | 98.0 2.0 | MgO 1.0 | 75.0 | 25.0 | $2.8\times10^9$ | $6.2\times10^4$ | $4.5\times10^4$ | $2.8\times10^9$ | $6.2\times10^4$ | 1.0 |
| 67 | Cr$_2$O$_3$ SiO$_2$ | 98.0 2.0 | MgO 1.0 | 75.0 | 25.0 | $3.0\times10^9$ | $6.1\times10^4$ | $4.9\times10^4$ | $3.0\times10^9$ | $6.2\times10^4$ | 1.0 |

*(outside the invention)

What is claimed is:

1. A humidity sensitive ceramic resistor comprising a ceramic plate having a conductive electrode secured to a surface thereof; said ceramic plate consisting essentially of, as solid ingredients, more than 98 to 99.95 percent by weight of main component consisting essentially of 99.99 to 80 percent by mole of chromium oxide (Cr$_2$O$_3$) and 0.01 to 20 percent by mole of at least one metal oxide selected from the group consisting of titanium oxide, zirconium oxide, hafnium oxide, tin oxide, niobium oxide, tantalum oxide, tungsten oxide, manganese oxide, molybdenum oxide, cerium oxide, dysprosium oxide, vanadium oxide, silicon oxide and germanium oxide; and 0.05 to less than 2 percent by weight of an additive of at least one metal oxide selected from the group consisting of beryllium oxide, magnesium oxide, calcium oxide, strontium oxide, barium oxide, iron oxide, nickel oxide, copper oxide, zinc oxide, cadmium oxide and lead oxide.

2. A humidity sensitive ceramic resistor according to claim 1, wherein said additive consists essentially of magnesium oxide.

3. A humidity sensitive ceramic resistor according to claim 1, wherein said additive consists essentially of iron oxide.

4. A humidity sensitive ceramic resistor according to claim 1, wherein said additive consists essentially of nickel oxide.

5. A humidity sensitive ceramic resistor according to claim 1 wherein said additive consists essentially of zinc oxide.

6. A humidity sensitive ceramic resistor according to claim 1, wherein said conductive electrode comprises a metal oxide semiconductor having a lower electrical resistance than that of said ceramic plate.

7. A humidity sensitive ceramic resistor according to claim 6, wherein said conductive electrode comprises at least one metal oxide semiconductor selected from the group consisting of ruthenium oxide, nickel oxide, tin oxide, indium oxide, cadmium oxide, titanium oxide, zinc oxide, barium titanate and barium metaplumbate.

8. A humidity sensitive ceramic resistor according to claim 7, wherein said conductive electrode comprises ruthenium oxide.

9. A humidity sensitive thin layer ceramic resistor comprising a thin layer ceramic film coated onto an insulating ceramic material having a conductive electrode secured to a surface thereof; said thin layer ceramic film consisting essentially of 97 to 20 percent by weight of humidity sensitive resistor component and 3 to 80 percent by weight of glass frit binder; said humidity sensitive resistor component consisting essentially of, as solid ingredients, 99.50 to 80 percent by weight of main component consisting essentially of 99.99 to 80 percent by mole of chromium oxide ($Cr_2O_3$) and 0.01 to 20 percent by mole of at least one metal oxide selected from the group consisting of titanium oxide, zirconium oxide, hafnium oxide, tin oxide, niobium oxide, tantalum oxide, tungsten oxide, manganese oxide, molybdenum oxide, cerium oxide, dysprosium oxide, vanadium oxide, silicon oxide and germanium oxide; and 0.05 to 20 percent by weight of an additive of at least one metal oxide selected from the group consisting of beryllium oxide, magnesium oxide, calcium oxide, strontium oxide, barium oxide, iron oxide, nickel oxide, copper oxide, zinc oxide, cadmium oxide and lead oxide.

10. A humidity sensitive thin layer ceramic resistor according to claim 9, wherein said glass frit binder comprises at least one metal compound selected from the group consisting of lead silicate, boron silicate, lead boron silicate and lead boron silicate containing at least one metal oxide selected from the group consisting of alkali earth metal oxides, zinc oxide and cadmium oxide.

11. A humidity sensitive thin layer ceramic resistor according to claim 9, wherein said additive consists essentially of magnesium oxide.

12. A humidity sensitive thin layer ceramic resistor according to claim 9, wherein said additive consists essentially of iron oxide.

13. A humidity sensitive thin layer ceramic resistor according to claim 9, wherein said additive consists essentially of nickel oxide.

14. A humidity sensitive thin layer ceramic resistor according to claim 9, wherein said additive consists essentially of zinc oxide.

15. A humidity sensitive thin layer ceramic resistor according to claim 9, wherein said conductive electrode comprises a metal oxide semiconductor having a lower electrical resistance than that of said ceramic film.

16. A humidity sensitive thin layer ceramic resistor according to claim 15, wherein said conductive electrode comprises at least one metal oxide semiconductor selected from the group consisting of ruthenium oxide, nickel oxide, tin oxide, indium oxide, cadmium oxide, titanium oxide, zinc oxide, barium titanate and barium metaplumbate.

17. A humidity sensitive thin layer ceramic resistor according to claim 16, wherein said conductive electrode comprises ruthenium oxide.

* * * * *